United States Patent [19]

Hori et al.

[11] Patent Number: 4,459,407
[45] Date of Patent: Jul. 10, 1984

[54] 1-(4-AMINOBENZYL)-2,3-DIOXOPIPERAZINE DERIVATIVES AND SALTS THEREOF

[75] Inventors: Takako Hori, Toyama; Chosaku Yoshida, Takaoka; Yasuo Kiba, Toyama; Ryuko Takeno, Toyama; Joji Nakano, Toyama; Jun Nitta, Namekawa; Sumiko Kishimoto, Toyama; Shohachi Murakami, Toyama; Hisatsugu Tsuda, Toyama; Isamu Saikawa, Toyama, all of Japan

[73] Assignee: Toyama Chemical Co., Ltd., Tokyo, Japan

[21] Appl. No.: 345,055

[22] Filed: Feb. 2, 1982

Related U.S. Application Data

[63] Continuation-in-part of Ser. No. 169,457, Jul. 16, 1980.

[30] Foreign Application Priority Data

Jul. 24, 1979 [JP] Japan ............................. 54-93234
Feb. 6, 1981 [JP] Japan ............................. 56-15837

[51] Int. Cl.³ ............... C07D 403/10; C07D 403/12; A61K 31/505; A61K 31/495
[52] U.S. Cl. ............................... 544/295; 544/179; 544/212; 544/238; 544/347; 544/360; 544/366; 544/374; 424/249; 424/250; 424/251
[58] Field of Search ............... 544/347, 238, 360, 295

[56] References Cited

U.S. PATENT DOCUMENTS 4,110,327  8/1978  Sarkawa et al. .................... 544/369

OTHER PUBLICATIONS

Hori et al., Chem. and Pharm. Bulletin, vol. 29, (3) pp. 684–698, (1981), (I).
Hori et al., Chem. and Pharm. Bulletin, vol. 29, (6), pp. 1594–1605, (1981) (II).

Primary Examiner—Donald G. Daus
Assistant Examiner—S. A. Gibson
Attorney, Agent, or Firm—Oblon, Fisher, Spivak, McClelland & Maier

[57] ABSTRACT

A 1-(4-aminobenzyl)-2,3-dioxopiperazine derivative represented by the formula:

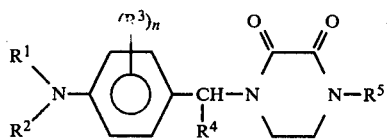

and a salt thereof have excellent carcinostatic activity but a low toxicity. Therefore, said compounds are useful as medicines and also as intermediates.

5 Claims, No Drawings

1-(4-AMINOBENZYL)-2,3-DIOXOPIPERAZINE DERIVATIVES AND SALTS THEREOF

CROSS-REFERENCES TO RELATED APPLICATIONS

This is a continuation-in-part of application Ser. No. 169,457, filed on July 16, 1980.

BACKGROUND OF THE INVENTION

1. Field of the Invention

This invention relates to novel 1-(4-aminobenzyl)-2,3-dioxopiperazine derivatives and salts thereof.

The compounds of this invention are per se excellent in carcinostatic activity, low in toxicity, useful as medicines, and useful also as intermediates.

2. Summary of the Invention

An object of this invention is to provide novel 1-(4-aminobenzyl)-2,3-dioxopiperazine derivatives having 1-(4-aminobenzyl)-2,3-dioxopiperazinyl moiety in their molecules, and salts thereof.

Another object of this invention is to provide novel 1-(4-aminobenzyl)-2,3-dioxopiperazine derivatives which have a carcinostatic activity and are low in toxicity, and salts thereof.

Other objects and advantages of this invention will be apparent from the following description.

According to this invention, there is provided a novel 1-(4-aminobenzyl)-2,3-dioxopiperazine derivative represented by the formula (I), or the salt thereof,

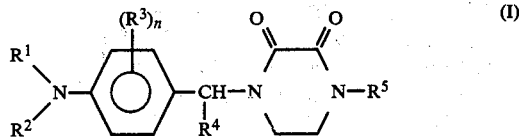

wherein either $R^1$ or $R^2$ represents a substituted or unsubstituted alkyl group, and the other represents a substituted or unsubstituted 6-membered heterocyclic group; n is 0, 1 or 2; $nR^3$'s may be the same or different and independently represent a halogen atom, an amino group, or a substituted or unsubstituted alkyl, alkoxy, alkylamino or dialkylamino group; $R^4$ represents a hydrogen atom or a substituted or unsubstituted alkyl group; and $R^5$ represents a hydrogen atom or a substituted or unsubstituted alkyl, alkenyl, alkadienyl, cycloalkyl, aralkyl, aryl or heterocyclic group.

DETAILED DESCRIPTION OF THE INVENTION

In the formula (I), $R^1$ and $R^2$ may be alkyl, preferably $C_{1-8}$alkyl, such as, for example, methyl, ethyl, propyl, isopropyl, butyl, pentyl, hexyl, heptyl, octyl, and the like; and 6-membered heterocyclic, preferably saturated or unsaturated 6-membered heterocyclic groups containing at least one hetero atom selected from the group consisting of O, S and N, such as, for example, piperidinyl, 2-pyridyl, 3-pyridyl, 4-pyridyl, 2-pyrimidinyl, 4-pyrimidinyl, 5-pyrimidinyl, 3-pyridazinyl, 4-pyridazinyl, pyrazinyl, triazinyl, and the like.

The above-mentioned 6-membered heterocyclic groups for $R^1$ and $R^2$ may be substituted by at least one substituent selected from the group consisting of halogen atoms such as fluorine, chlorine, bromine, and iodine; hydroxyl group; carboxyl group; $C_{1-4}$alkoxycarbonyl groups such as methoxycarbonyl, ethoxycarbonyl, and the like; ar-$C_{1-4}$alkoxycarbonyl groups such as benzyloxycarbonyl and the like; aryloxycarbonyl groups such as phenoxycarbonyl and the like; $C_{1-4}$alkyl groups such as methyl, ethyl, propyl, isopropyl, butyl and the like; di-$C_{1-4}$-alkoxy-$C_{1-4}$alkyl groups such as dimethoxyethyl, diethoxyethyl and the like; $C_{2-4}$alkenyl groups such as vinyl, allyl and the like; ar-$C_{1-4}$alkyl groups such as benzyl, phenethyl and the like; $C_{5-6}$cycloalkyl groups such as cyclopentyl, cyclohexyl and the like; cyano group; mercapto group; $C_{1-4}$alkylthio groups such as methylthio, ethylthio and the like; nitro group; oxo group; imino group; thioxo group; $C_{1-4}$alkanoylamino groups such as acetamido and the like; $C_{1-4}$alkoxy groups such as methoxy, ethoxy, butoxy and the like; ar-$C_{1-4}$alkyloxy groups such as benzyloxy and the like; $C_{1-8}$acyl groups such as formyl, acetyl, propionyl, butyryl, benzoyl and the like; amino group; $C_{1-4}$alkylamino groups such as methylamino, ethylamino, propylamino and the like; di-$C_{1-4}$alkylamino groups such as dimethylamino, diethylamino, dipropylamino and the like; arylamino groups such as anilino and the like; ar-$C_{1-4}$alkylamino groups such as benzylamino, dimethylaminobenzylamino, diethylaminobenzylamino, phenethylamino and the like; heterocyclic amino groups such as pyridylamino, pyrimidinylamino and the like; and heterocyclic groups such as piperidinyl, 2-pyridyl, 3-pyridyl, 4-pyridyl, 2-pyrimidinyl, 4-pyrimidinyl, 5-pyrimidinyl, 3-pyridazinyl, 4-pyridazinyl, pyrazinyl, triazinyl, 2-pyrrolidinyl, 3-pyrrolidinyl, 3-pyrazolyl, 4-pyrazolyl, 5-pyrazolyl, 4-triazolyl, 5-triazolyl, 5-tetrazolyl, 2-thienyl, 3-thienyl, 2-furyl, 3-furyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, 2-imidazolyl, 4-imidazolyl, 5-imidazolyl, 2-indolyl, 3-indolyl, 5-indolyl, 2-benzimidazolyl, 5-benzimidazolyl and the like. The above-mentioned alkyl group for $R^1$ and $R^2$ may be substituted by at least one substituent selected from the group consisting of the substituents as defined above; and $C_{5-6}$cycloalkyloxy groups such as cyclopentyloxy, cyclohexyloxy and the like; $C_{5-6}$cycloalkylthio groups such as cyclopentylthio, cyclohexylthio and the like; ar-$C_{1-4}$alkylthio groups such as benzylthio, phenethylthio and the like; $C_{2-4}$alkenyloxy groups such as vinyloxy, allyloxy and the like; $C_{2-4}$alkenylthio groups such as vinylthio, allylthio and the like; $C_{4-10}$alkadienyloxy groups such as 1,3-butadienyloxy, 2,4-hexadienyloxy, geranyloxy and the like; $C_{4-10}$alkadienylthio groups such as 1,3-butadienylthio, 2,4-hexadienylthio and the like; aryloxy groups such as phenoxy, naphthoxy and the like; arylthio groups such as phenylthio, naphthylthio and the like; acyloxy groups such as acetyloxy, propionyloxy, butyryloxy, pivaloyloxy, stearoyloxy, benzoyloxy, furoyloxy, thenoyloxy, pyridylcarbonyloxy, cyclohexylcarbonyloxy and the like; and acylthio groups such as acetylthio, propionylthio, butyrylthio, pivaloylthio, stearoylthio, benzoylthio, furoylthio, thenoylthio, pyridylcarbonylthio, cyclohexylcarbonylthio and the like.

Further, the above-mentioned substituents of the alkyl group for $R^1$ and $R^2$ may be substituted by at least one substituent selected from the group consisting of halogen atoms such as fluorine, chlorine, bromine and iodine; hydroxyl group; carboxyl group; $C_{1-4}$alkoxycarbonyl groups such as methoxycarbonyl, ethoxycarbonyl and the like; ar-$C_{1-4}$alkyloxycarbonyl groups such as benzyloxycarbonyl and the like; aryloxycarbonyl groups such as phenoxycarbonyl and the like; $C_{1-4}$alkyl groups such as methyl, ethyl, n-propyl, isopropyl, butyl and the like; $C_{2-4}$alkenyl groups such as vinyl, allyl and the like; ar-$C_{1-4}$alkyl groups such as benzyl, phenethyl and the like; $C_{5-6}$cycloalkyl groups such as cyclopentyl, cyclohexyl and the like; cyano group; mercapto group; $C_{1-4}$alkylthio groups such as methylthio, ethylthio and the like; nitro group; oxo group; acylamino groups such as acetamido and the like; $C_{1-4}$alkoxy groups such as methoxy, ethoxy and the like; ar-$C_{1-4}$alkyloxy groups such as benzyloxy and the like; acyl groups such as formyl, acetyl, propionyl, butyryl, benzoyl and the like; amino group; $C_{1-4}$alkylamino groups such as methylamino, ethylamino, hydroxyethylamino, propylamino and the like; di-$C_{1-4}$alkylamino groups such as dimethylamino, diethylamino, bis(hydroxyethyl)amino, dipropylamino and the like; arylamino groups such as anilino and the like; ar-$C_{1-4}$alkylamino groups such as benzylamino, phenethylamino and the like; heterocyclic groups such as the same heterocyclic groups mentioned above for $R^1$ and $R^2$; and heterocyclic amino groups such as pyridylamino, pyrimidinylamino and the like.

The halogen atom, alkyl group, alkoxy group, alkylamino group and dialkylamino group for $R^3$ and the alkyl group for $R^4$ include the same specific examples mentioned for $R^1$ and $R^2$. $R^3$ and $R^4$ may be substituted by the same substituents as mentioned for the substituents of the alkyl group for $R^1$ and $R^2$.

$R^5$ is an alkyl group, preferably $C_{1-8}$alkyl, such as methyl, ethyl, propyl, butyl, pentyl, hexyl, heptyl, octyl, or the like; an alkenyl group, preferably $C_{2-4}$alkenyl, such as vinyl, allyl, or the like; an alkadienyl group, preferably $C_{4-10}$alkadienyl, such as 1,3-butadienyl, 2,4-hexadienyl, geranyl, or the like; a cycloalkyl group, preferably $C_{5-6}$cycloalkyl, such as cyclopentyl, cyclohexyl, or the like; an aralkyl group, preferably ar-$C_{1-4}$alkyl, such as benzyl, phenethyl, or the like; an aryl group, such as phenyl, naphthyl, or the like; and a heterocyclic group, which includes the same specific examples as metnioned for $R^1$ and $R^2$. $R^5$ may be substituted by at least one substituent selected from the group consisting of the substituents mentioned above for the substituents of the alkyl group for $R^1$ and $R^2$; and ar-$C_{1-4}$alkoxy groups such as benzyloxy, phenethyloxy, and the like, and $C_{5-6}$cycloalkylamino groups such as cyclopentylamino, cyclohexylamino, and the like. When $R^5$ is substituted by a heterocyclic group, the heterocyclic group may be substituted by the same substituent as mentioned above for the substituents of the alkyl group for $R^1$ and $R^2$.

Among the groups listed above, there are preferred combinations of $R^5$ which is a substituted or unsubstituted alkyl or aralkyl group with $R^2$ which is the group represented by the formula,

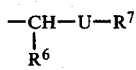

wherein $R^6$ represents a hydrogen atom or a $C_{1-7}$alkyl group; $R^7$ represents a $C_{1-8}$alkyl, $C_{5-6}$cycloalkyl, ar-$C_{1-4}$alkyl, $C_{2-4}$alkenyl, $C_{4-10}$alkadienyl, aryl or acyl group which may be substituted by at least one substituent mentioned above for the substituents of the alkyl group for $R^1$ and $R^2$; and U represents an oxygen atom or a sulfur atom. Further, a combination of $R^4$ which is a hydrogen atom with $R^5$ which is a substituted or unsubstituted alkyl or aralkyl group is preferred.

For the formation of the salts of the compounds represented by the formula (I), any acids or bases may be used so long as the resulting salts are pharmaceutically acceptable, though inorganic or organic acidic salts such as salts with hydrogen chloride, hydrogen bromide, sulfuric acid, phosphoric acid, p-toluenesulfonic acid salt, and the like and inorganic or organic basic salts such as salts with potassium, sodium, calcium, ammonium, pyridine, collidine, triethylamine, triethanolamine, procaine, and the like are particularly preferred. Hydrates of the compounds represented by the formula (I) and hydrates of the salts of the compunds of the formula (I) are also included in this invention.

The carbinostatic activity and acute toxicity of the representative compounds of this invention are explained below.

A. Antitumor Effect a. MIC value against HeLa S3 cells and Ehrlich cells (microplate method)
Number of cells: $2 \times 10^4$ cells/ml
Culture medium: Eagle's MEM+20% calf embryonic serum
Culture time: 4 days
Judgement: Giemsa staining

TABLE 1

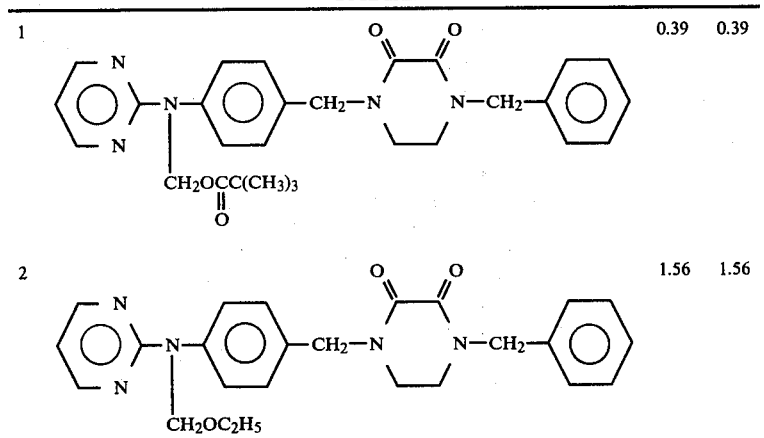

TABLE 1-continued

| # | Structure | | |
|---|---|---|---|
| 3 | 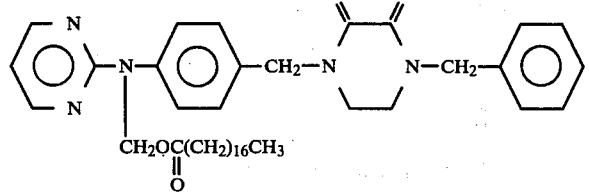 | 0.39 | 0.39 |
| 4 | 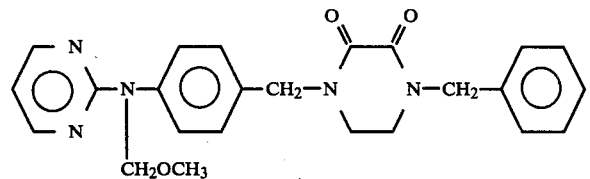 | 1.56 | 3.13 |
| 5 | 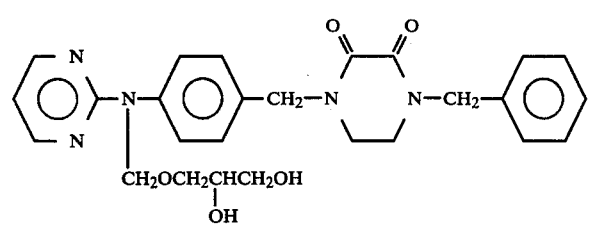 | 3.13 | 3.13 |
| 6 | 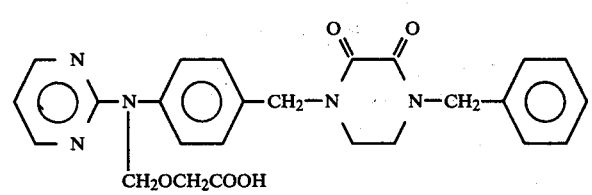 | 0.39 | 0.78 |
| 7 | 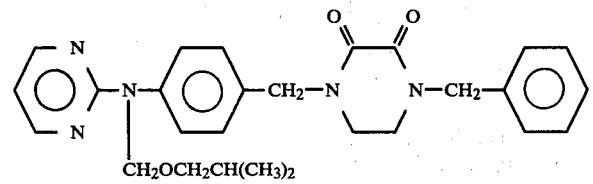 | 3.13 | 6.25 |
| 8 | 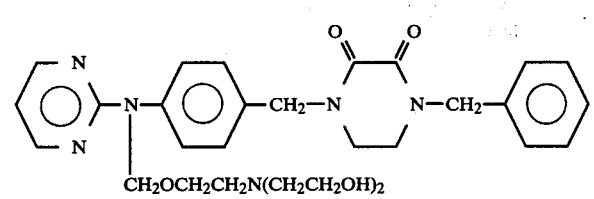 | 12.5 | 12.5 | b. Effect on L-1210 Leukemia

L-1210 cells ($1 \times 10^5$ cells/head) were inoculated subcutaneously into $BDF_1$-strain mice (male, 7 weeks old, each group consisting of 5 mice) and after 24 hours, test drugs were orally administered once a day for 7 successive days. The effect thereof was judged from the mean survival days.

The test drugs were used in the form of a solution or suspension in a saline solution or a 0.3% carboxymethyl cellulose-containing saline solution.

$$T/C = \frac{\text{Mean survival days in group to which test drug was administered}}{\text{Mean survival days of control group}} \times 100(\%)$$

TABLE 2

| Compound No. | Dose (mg/kg/day) | T/C (%) |
|---|---|---|
| 1 | 50 | 135 |
|   | 100 | 162 |
| 2 | 110 | 120 |
|   | 220 | 237 |
| 4 | 110 | 177 |
|   | 220 | 289 |
| 5 | 65 | 140 |
|   | 130 | 177 |
| 7 | 120 | 118 |
|   | 240 | 177 |

B. Acute Toxicity

Each of the test drugs was administered orally once to ICR-strain mice (male, 7 weeks old, each group consisting of 5 mice), and the mice were observed for 7 days, to obtain the results shown in Table 3.

The test drugs were used in the form of a solution or suspension in a saline solution or a 0.3% carboxymethyl cellulose-containing saline solution.

TABLE 3

| Compound No. | LD$_{50}$ (mg/kg) |
| --- | --- |
| 1 | >2000 |
| 2 | >2000 |
| 4 | >2000 |
| 5 | >2000 |
| 7 | >2000 |

From the results shown above, it can be seen that the compounds represented by the formula (I) have such excellent properties that they are effective in any administration form against various tumors and are low in toxicity, and hence, they are very useful.

A detailed explanation is made below of processes for producing the present compounds represented by the formula (I).

Production process (1)

A process for producing a 1-(4-aminobenzyl)-2,3-dioxopiperazine derivative represented by the formula (IV), or a salt thereof,

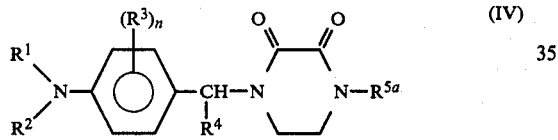

wherein $R^1$, $R^2$, $R^3$, $R^4$ and n have the same meanings as defined above and $R^{5a}$ is a substituted or unsubstituted alkyl, alkenyl, alkadienyl, cycloalkyl, aralkyl, aryl or heterocyclic group, which comprises reacting a compound represented by the formula (II), or a reactive derivative thereof,

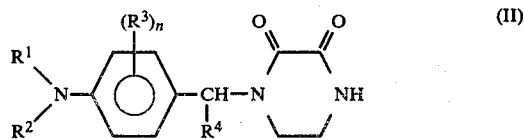

wherein $R^1$, $R^2$, $R^3$, $R^4$ and n have the same meanings as defined above, with a compound represented by the formula (III),

wherein $R^{5a}$ has the same meaning as defined above, and Y represents a reactive group.

Production process (2)

A process for producing a 1-(4-aminobenzyl)-2,3-dioxopiperazine derivative repesented by the formula (I), or a salt thereof,

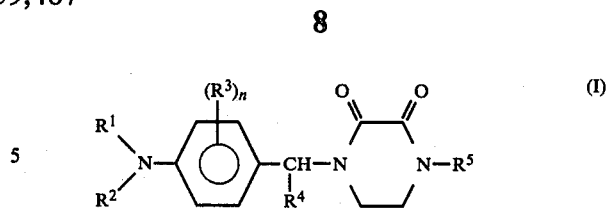

wherein $R^1$, $R^2$, $R^3$, $R^4$, $R^5$ and n have the same meanings as defined above, which comprises reacting a compound represented by the formula (V),

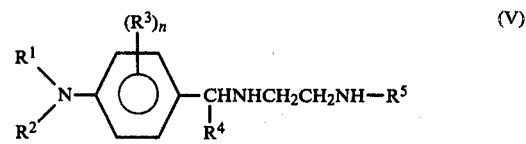

wherein $R^1$, $R^2$, $R^3$, $R^4$, $R^5$ and n have the same meanings as defined above, with an oxalic acid derivative represented by the formula (VI), $$\begin{matrix} COX \\ | \\ COX \end{matrix} \quad (VI)$$

wherein X represents a reactive group.

Production process (3)

A process for producing a 1-(4-aminobenzyl)-2,3-dioxopiperazine derivative represented by the formula (IV), or a salt thereof,

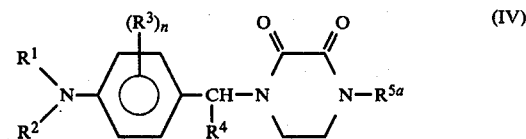

wherein $R^1$, $R^2$, $R^3$, $R^4$, $R^{5a}$ and n have the same meanings as defined above, which comprises reacting a compound represented by the formula (VII), or a reactive derivative thereof,

wherein $R^{5a}$ has the same meaning as defined above, with a compound represented by the formula (VIII),

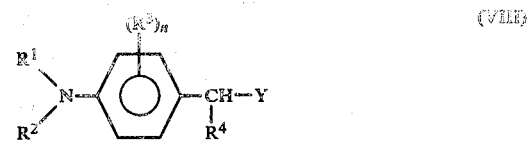

wherein $R^1$, $R^2$, $R^3$, $R^4$, n and Y have the same meanings as defined above.

Production process (4)

A process for producing a 1-(4-aminobenzyl)-2,3-dioxopiperazine derivative represented by the formula (I), or a salt thereof,

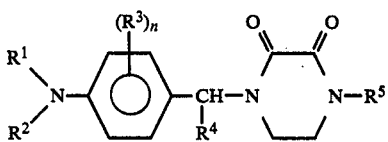

wherein $R^1$, $R^2$, $R^3$, $R^4$, $R^5$ and n have the same meanings as defined above, provided that $R^2$ represents a substituted or unsubstituted alkyl group when $R^1$ is a substituted or unsubstituted 6-membered heterocyclic group, or represents a substituted or unsubstituted 6-membered heterocyclic group when $R^1$ is a substituted or unsubstituted alkyl group, which comprises reacting a compound represented by the formula (IX), or a reactive derivative thereof,

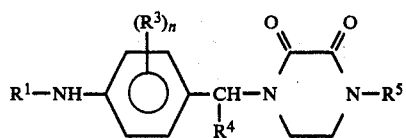

wherein $R^1$, $R^3$, $R^4$, $R^5$ and n have the same meanings as defined above, with a compound represented by the formula (X),

wherein $R^2$ has the same meaning as defined above, and $Y^1$ represents a reactive group.

Production process (5)

A process for producing a 1-(4-aminobenzyl)-2,3-dioxopiperazine derivative represented by the formula (XI), or a salt thereof,

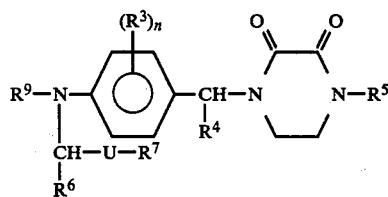

wherein $R^9$ represents a substituted or unsubstituted 6-membered heterocyclic group, and $R^3$, $R^4$, $R^5$, $R^6$, $R^7$, U and n have the same meanings as defined above, which comprises reacting a compound represented by the formula (XII),

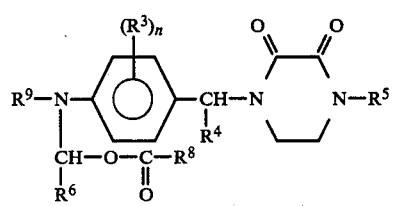

wherein $R^3$, $R^4$, $R^5$, $R^6$, $R^9$ and n have the same meanings as defined above and $R^8$ represents an unsubstituted or substituted alkyl, cycloalkyl, aralkyl, alkenyl, alkadienyl or aryl group, with a compound represented by the formula (XIII),

wherein $R^7$ and U have the same meanings as defined above.

The compound of this invention can be produced by, for example, the above-mentioned 5 processes. In each of the processes, $R^1$, $R^2$, $R^3$, $R^4$, $R^5$ and n have the same meanings as defined above. $R^{5a}$ in the formulas (III), (IV) and (VII) include the same alkyl, alkenyl, alkadienyl, cycloalkyl, aralkyl, aryl and heterocyclic groups as mentioned for $R^5$, and may be substituted by the same substituents as mentioned for $R^5$.

As the reactive group for Y in the formulas (III) and (VIII), there may be mentioned halogen atoms such as chlorine, bromine, iodine, and the like; arylsulfonyloxy groups such as p-toluenesulfonyloxy, phenylsulfonyloxy, and the like; and alkylsulfonyloxy groups such as methanesulfonyloxy, ethanesulfonyloxy, and the like. As the reactive group for X in the formula (VI), in which X's may be the same or different, there may be mentioned, for example, alkoxy groups such as methoxy, ethoxy, and the like; and halogen atoms such as chlorine and the like.

$R^8$ in the formula (XII) includes the same $C_{1-8}$alkyl, $C_{5-6}$cycloalkyl, ar-$C_{1-4}$alkyl, $C_{2-4}$alkenyl, $C_{4-10}$alkadienyl and aryl groups mentioned for $R^7$, and $R^8$ may be substituted by the same substituents as mentioned for $R^7$.

$R^9$ in the formulas (XI) and (XII) includes the same 6-membered heterocyclic groups mentioned for $R^1$ and $R^2$, and $R^9$ may be substituted by the same substituents as mentioned for $R^1$ and $R^2$.

As the reactive group for $Y^1$ in the formulas (X), there may be mentioned halogen atoms such as chlorine, bromine, iodine, and the like; arylsulfonyloxy groups such as p-toluenesulfonyloxy, phenylsulfonyloxy, and the like; alkylsulfonyloxy groups such as methanesulfonyloxy, ethanesulfonyloxy, and the like; alkoxy groups such as methoxy, ethoxy, and the like; and alkylthio groups such as methylthio, ethylthio, and the like.

In each of the above-mentioned production methods, the reactive derivatives of the compounds represented by the formulas (II), (VII) and (IX) include compounds formed by bonding an alkali metal atom such as lithium, sodium, potassium, or the like; a silyl group such as $(CH_3)_3Si-$, $(CH_3)_2Si<$, $(CH_3)_2[(CH_3)_2CH]Si-$, $(CH_3O)_3Si-$, $CH_3(CH_3O)_2Si-$, $(CH_3)_2(CH_3O)Si-$, or the like; or a phosphorus group such as

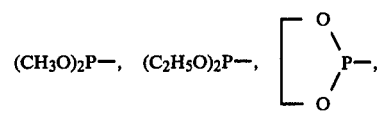

or the like, to the >NH or —$NH_2$ group which is a reaction site in the above-mentioned formulas. These reactive derivatives can easily be synthesized according to a conventional method, and may be subjected without isolation to the subsequent reaction.

The compounds represented by the formulas (II), (V), (IX) and (XII) which are the starting materials in the production method of this invention can be produced by various processes, among which representative are, for example, the above-mentioned processes of this invention and the processes which are through the following reaction routes:

Reaction Routes
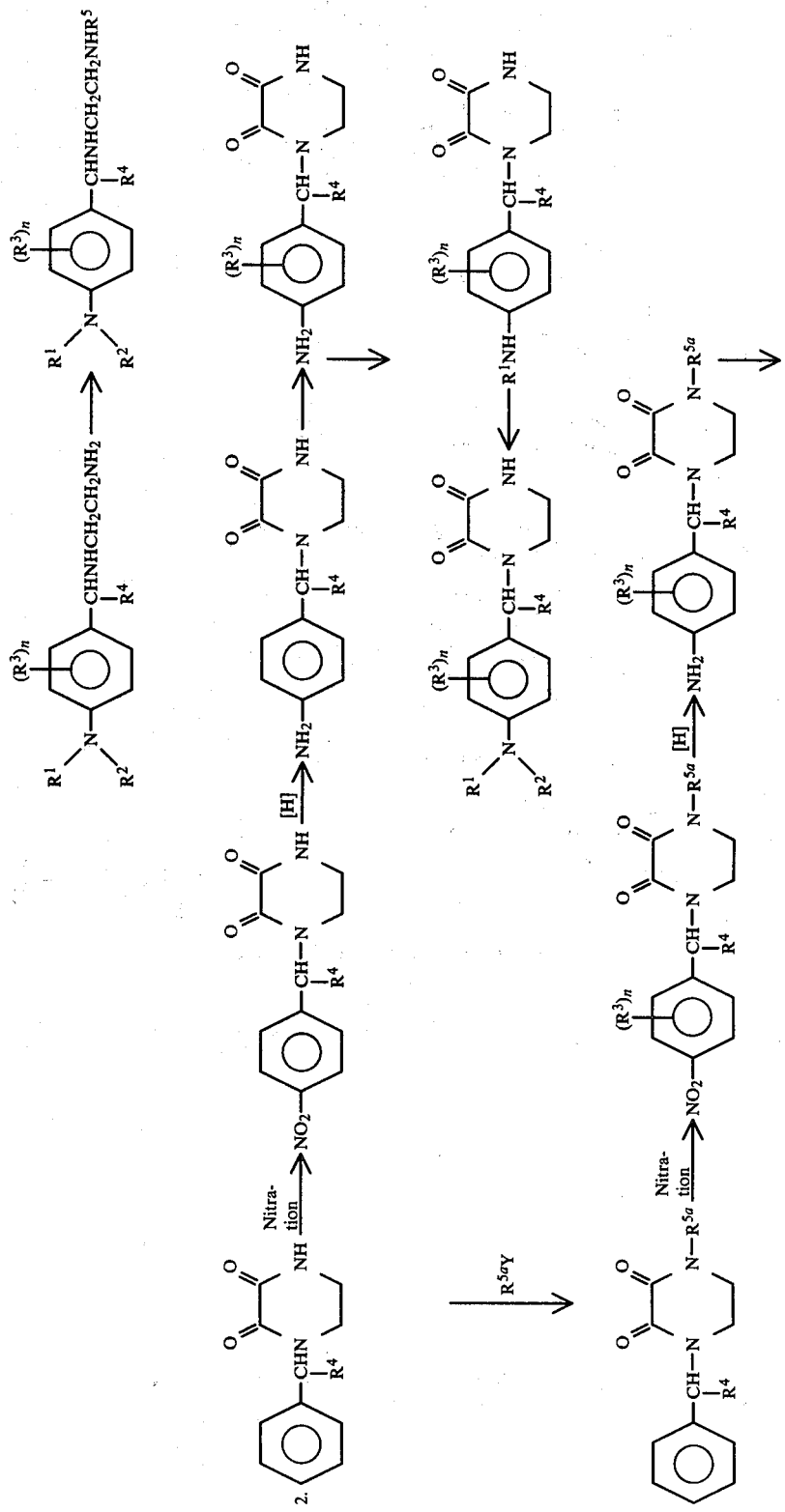

Reaction Routes
-continued
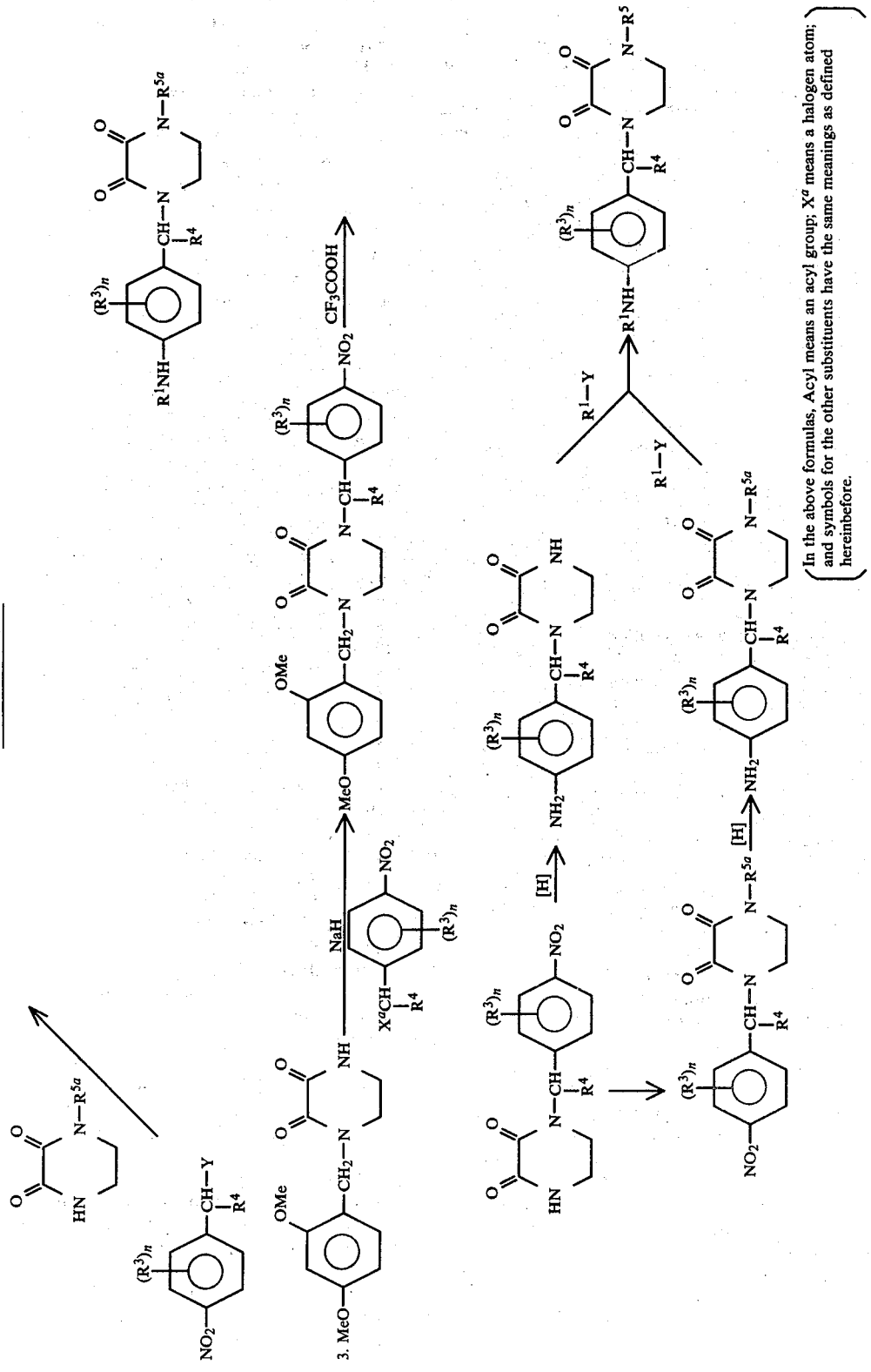

Embodiments of each production process are described below.

The production processes (1) and (3) are carried out similarly in the presence or absence of a solvent inert to the reaction. The solvent used in the reaction includes, for example, ethers such as tetrahydrofuran, diethyl ether, dimethoxyethyl ether, dimethoxyethane, dioxane, and the like; halogenated hydrocarbons such as methylene chloride, chloroform, 1,2-dichloroethane, and the like; alcohols such as methanol, ethanol, isopropanol, tert-butyl alcohol, tert-amyl alcohol, ethylene glycol, ethylene glycol monomethyl ether, and the like; amides such as dimethylformamide, dimethylacetamide, and the like; nitriles such as acetonitrile, propionitrile, and the like; aromatic hydrocarbons such as benzene, toluene, xylene, and the like; nitroalkanes such as nitromethane, nitroethane, and the like; tertiary amines such as pyridine, quinoline, and the like; sulfoxides such as dimethylsulfoxide and the like; and phosphoric amides such as hexamethylphosphoric amide and the like. The above-mentioned solvents may be used also in admixture of two or more.

The reaction temperature and the reaction time are not critical, though the reaction is preferably effected at 0° to 150° C., and in this case, the reaction is usually completed in 5 minutes to 12 hours. The reaction is usually effected at atmospheric pressure, though desirable results are sometimes obtained when the reaction is effected under pressure in a sealed tube or an autoclave. The compounds represented by the formulas (III) and (VII) are used in quantities at least equimolar to, preferably of 1.0 to 1.2 moles per mole of, the compounds represented by the formulas (II) and (VIII), respectively.

The production process (2) is carried out in the presence or absence of a solvent inert to the reaction. The solvent used in the reaction includes, for example, alcohols such as methanol, ethanol, isopropanol, and the like; ethers such as tetrahydrofuran, diethyl ether, dioxane, dimethoxyethane, and the like; aromatic hydrocarbons such as benzene, toluene, xylene, and the like; nitroalkanes such as nitromethane, nitroethane, and the like; nitriles such as acetonitrile, propionitrile, and the like; amides such as dimethylformamide, dimethylacetamide, and the like; and halogenated hydrocarbons such as methylene chloride, chloroform, and the like. These solvents may be used also in admixture of two or more. The reaction temperature and the reaction time are not critical, though the reaction is preferably effected at 0° to 150° C., and in this case, the reaction is usually completed in 30 minutes to 24 hours. The oxalic acid derivative represented by the formula (VI) is used in a quantity of usually 1 to 1.5 moles, preferably 1 to 1.2 moles, per mole of the compound represented by the formula (V).

The production process (4) is carried out in the presence or absence of a solvent inert to the reaction. The solvent used in the reaction is the same as used in the above-mentioned production methods (1) and (3). The reaction temperature and the reaction time are not critical though the reaction is preferably effected at room temperature to 150° C., and in this case, the reaction is completed in 5 minutes to 12 hours. The reaction is usually effected at atmospheric pressure, though desirable results are sometimes obtained when the reaction is effected under pressure in a sealed tube or an autoclave. The compound represented by the formula (X) is used in a quantity at least equimolar to, preferably of 1.0 to 2.0 moles per mole of, the compound represented by the formula (IX). In the production processes (1) to (4), a deacidifying agent or a catalyst may be used. In this case, as usable deacidifying agents, there may be mentioned, for example, tertiary amines such as triethylamine, pyridine, quinoline, N-methylmorpholine, diethylaniline, 4-dimethylaminopyridine, and the like; and inorganic bases such as potassium carbonate, sodium carbonate, sodium hydrogen carbonate, and the like. As the catalyst, metals such as activated copper and the like may be used.

The production process (5) is carried out in the presence or absence of a solvent inert to the reaction. The solvent used in the reaction includes, for example, ethers such as tetrahydrofuran, diethyl ether, dioxane, dimethoxyethane, and the like; aromatic hydrocarbons such as benzene, toluene, xylene, and the like; nitroalkanes such as nitromethane, nitroethane, and the like; nitriles such as acetonitrile, propionitrile, and the like; amides such as dimethylformamide, dimethylacetamide, and the like; halogenated hydrocarbons such as methylene chloride, chloroform, and the like; and fatty acids such as acetic acid, propionic acid, and the like. These solvents may be used also in admixture of two or more. The reaction temperature and the reaction time are not critical, though the reaction is preferably effected at 0° to 150° C., in this case, the reaction is usually completed in 30 minutes to 24 hours. The compound represented by the formula (XIII) is used in a quantity at least equimolar to the compound represented by the formula (XII).

When reacting the compound of the formula (XII) with the compound of the formula (XIII), a catalyst may be used. The catalyst includes, for example, protonic acids such as hydrogen chloride, hydrogen bromide, sulfuric acid, or the like; Lewis acids such as zinc chloride, aluminium chloride, tin chloride, titanium tetrachloride, boron trifluoride, or the like.

After the above production processes (1)–(5) are carried out in the manner described above, the compound represented by the formula (I) can be isolated from the reaction mixture according to a conventional method, and purified by procedures such as column chromatography, recrystallization, and the like. A salt of the compound represented by the formula (I) can be obtained by effecting the reaction according to a conventional method using an inorganic acid such as hydrochloric acid, hydrobromic acid, hydroiodic acid, or the like, an organic acid such as p-toluenesulfonic acid, acetic acid, or the like, an inorganic base such as potassium hydroxide, sodium hydroxide, sodium carbonate, sodium hydrogen carbonate, potassium hydrogen carbonate, aqueous ammonia, or the like, or an organic base such as pyridine, collidine, triethylamine, triethanolamine, procaine, or the like, and then isolating and purifying the reaction product. In the above-mentioned production methods, when the compounds represented by the formulas (II), (III), (V), (VII), (VIII), (IX), (X), (XII) and (XIII) have an active group such as amino, hydroxyl, carboxyl, or the like in the unreactive site, compounds having a protecting group can be obtained by protecting the active group with a well-known protecting group, and then carrying out the method of this invention, and a compound having a free active group can be obtained by treating the compound having a protecting group by a well-known method to release the protecting group.

The compounds represented by the formula (I) and their salts of this invention are applicable to various cancers, for example, solid tumor, leukemia, and the like. In using the compound of this invention, a carrier which is usually used in a carcinostatic agent may be added thereto, and the mixture is formulated into various drug forms, such as tablets, syrup, capsules, powder, an injection, and the like.

When the compound of this invention is actually administered to a man, the administration route, the dosage, and the number of administrations are properly selected depending upon the conditions of a patient, though, in general, it is sufficient that the compound is administered once to thrice a day in a dosage of 1 to 4000 mg/kg per day per adult by injection (intravenous injection, intramuscular injection, intraarterial injection, intravenous drip infusion, etc.) or orally. The compound of this invention may be administered either every day or intermittently, and may be used together with other carcinostatic agents.

DESCRIPTION OF THE PREFERRED EMBODIMENTS

This invention is further explained below referring to Examples, which are merely illustrative and not limitative.

EXAMPLE 1

In 5 ml of ethylene glycol were suspended 400 mg of 1-(4-ethylaminobenzyl)-4-n-hexyl-2,3-dioxopiperazine and 210 mg of 2-bromopyrimidine, and the resulting suspension was refluxed for 5 minutes. Subsequently, the suspension was allowed to stand at room temperature, and then extracted with 30 ml of chloroform, and the extract was washed successively with water and a saturated aqueous sodium chloride solution. The chloroform layer was dried over anhydrous magnesium sulfate, and the solvent was removed by distillation under reduced pressure. The residue thus obtained was purified by column chromatography (Wakogel C-200, eluted with chloroform), and then recrystallized from diethyl ether to obtain 100 mg (20.2% yield) of white crystals of 1-{4-[N-ethyl-N-(2-pyrimidinyl)]-aminobenzyl}-4-n-hexyl-2,3-dioxopiperazine having a melting point of 79° to 81° C.

IR (KBr) cm$^{-1}$:
$\nu_{C=O}$ 1673

EXAMPLE 2

(1) In 50 ml of N,N-dimethylformamide (referred to hereinafter as DMF) were dissolved 21.6 g of 2-bromopyrimidine and 30 g of 1-(4-aminobenzyl)-2,3-dioxopiperazine, and the resulting solution was subjected to reaction at 130° to 140° C. for 30 minutes. After the completion of the reaction, a saturated aqueous sodium hydrogen carbonate solution was added to the reaction mixture and the yellow crystals thus precipitated were collected by filtration. The crystals were recrystallized from hot water to obtain 28 g (68.8% yield) of pale yellow crystals of 1-[4-(2-pyrimidinylamino)benzyl]-2,3-dioxopiperazine having a melting poing of 253° C.

IR (KBr) cm$^{-1}$
$\nu_{NH}$ 3200, 3120
$\nu_{C=O}$ 1660

Elementary analysis (for $C_{15}H_{15}N_5O_2$) Calcd. (%) C: 60.59, H: 5.09, N: 23.56; Found (%) C: 60.25, H: 5.07, N: 23.10.

NMR(d$_6$-DMSO) ppm values:
3.45 (4H, bs, piperazine ring >CH$_2$×2)
4.61 (2H, s, >CH$_2$×1)
6.88 (1H, t, J=4.5 Hz, pyrimidine ring H×1)
7.30 (2H, d, J=8.5 Hz, benzene ring H×2)
7.84 (2H, d, J=8.5 Hz, benzene ring H×2)
8.52 (2H, d, J=4.5 Hz, pyrimidine ring H×2)
8.39–8.69 (1H, bs, >NH×1)
9.57 (1H, s, >NH×1)

(2) To a suspension of 480 mg of sodium hydride (50% purity) in 30 ml of DMF was added 3 g of 1-[4-(2-pyrimidinylamino)benzyl]-2,3-dioxopiperazine with stirring, and the resulting mixture was subjected to reaction at room temperature for 30 minutes. Subsequently, a suspension of 1.4 g of benzyl chloride in 5 ml of DMF was added dropwise to the reaction mixture, and the mixture thus obtained was further subjected to reaction at 80° to 90° C. for one hour. After the completion of the reaction, the solvent was removed by distillation under reduced pressure, and the residue obtained was extracted with 100 ml of chloroform, and the extract was then washed with water. The chloroform layer was dried over anhydrous magnesium sulfate, after which the solvent was removed by distillation under reduced pressure, and the crystals thus obtained were recrystallized from ethanol to obtain 3.5 g (90% yield) of yellow crystals of 1-benzyl-4-[4-(2-pyrimidinylamino)benzyl]-2,3-dioxopiperazine having a melting point of 175° to 176° C.

IR (KBr) cm$^{-1}$:
$\nu_{NH}$ 3320
$\nu_{C=O}$ 1670

Elementary analysis (for $C_{22}H_{21}N_5O_2$) Calcd. (%) C: 68.20, H: 5.46, N: 18.08; Found (%) C: 68.24, H: 5.38, N: 17.89.

NMR (d$_6$-DMSO) ppm values:
3.42 (4H, bs, piperazine ring >CH$_2$×2)
4.51 (2H, s, >CH$_2$×1)
4.54 (2H, s, >CH$_2$×1)
6.75 (1H, t, J=4.5 Hz, pyrimidine ring H×1)
7.15 (2H, d, J=8.5 Hz, benzene ring H×2)
7.25 (5H, s, benzene ring H×5)
7.70 (2H, d, J=8.5 Hz, benzene ring H×2)
8.40 (2H, d, J=4.5 Hz, pyrimidine ring H×2)
9.68 (1H, s, >NH×1)

(3) To a mixture of 372 mg of sodium hydride (purity 50%) and 30 ml of N,N-dimethylformamide was added dropwise a solution of 3 g of 1-benzyl-4-[4-(2-pyrimidinylamino)benzyl]-2,3-dioxopiperazine in 20 ml of N,N-dimethylformamide with stirring over 30 min., after which the resulting mixture was subjected to reaction at 60° to 70° C. for one hour. After the completion of the reaction, 1.3 g of pivaloyloxymethyl chloride was dropped thereinto over 10 min. at the same temperature. After the completion of the dropwise addition, the resulting mixture was subjected to reaction at 70° to 80° C. for 30 min. After the completion of the reaction, the solvent was removed by distillation under reduced pressure, and the residue thus obtained was extracted with 100 ml of chloroform. The chloroform layer was washed with 30 ml of water and 40 ml of saturated aqueous sodium chloride solution in this order, and dried over anhydrous magnesium sulfate, after which the solvent was removed by distillation under reduced pressure. The residue thus obtained was purified by column chromatography (Wakogel C-200, eluted with chloroform), and then recrystallized from ethyl acetate-diisopropyl ether, to obtain 2.5 g (64.3% yield) of 1-benzyl-4-{4-[N-pivaloyloxymethyl-N-(2-pyrimidinyl)amino]benzyl}-2,3-dioxopiperazine having a melting point of 144° to 146° C.

IR (KBr) cm$^{-1}$:
  $\nu_{C=O}$ 1725, 1670

Elementary analysis (for $C_{28}H_{31}N_5O_4$) Calcd. (%) C: 67.05, H: 6.23, N: 13.96; Found (%) C: 66.99; H: 6.23, N: 13.85.

NMR (CDCl$_3$) ppm values:
  1.17 (9H, s, CH$_3 \times$3)
  3.38 (4H, s, piperazine ring CH$_2 \times$2)
  4.65 (4H, s, CH$_2 \times$2)
  5.95 (2H, s, CH$_2 \times$1)
  6.68 (1H, t, J=5.0 Hz, pyrimidine ring H$\times$1)
  7.23 (4H, s, benzene ring H$\times$4)
  7.25 (5H, s, benzene ring H$\times$5)
  8.33 (2H, d, J=5.0 Hz, pyrimidine ring H$\times$2).

EXAMPLE 3

In 30 ml of ethyl acetate was dissolved 1 g of 1-benzyl-4-{4-[N-pivaloyloxymethyl-N-(2-pyrimidinyl)-amino]benzyl}-2,3-dioxopiperazine, and 1 g of glycolic acid and 0.02 ml of N hydrogen chloride-ethanol solution were added, after which the resulting mixture was subjected to reaction at room temperature for 3 hours with stirring. After the completion of the reaction, the solvent was removed by distillation under reduced pressure, and the residue thus obtained was extracted with 100 ml of methylene chloride. The methylene chloride layer was washed with 30 ml of water and then 30 ml of saturated aqueous sodium chloride solution, and dried over anhydrous magnesium sulfate, after which the solvent was removed by distillation under reduced pressure. The residue thus obtained was purified by a column chromatography (Wakogel C-200, eluted with chloroformethanol), and recrystallized from ethyl acetate-diisopropyl ether, to obtain 0.5 g (52.8% yield) of 1-benzyl-4-{4-[N-carboxymethoxymethyl-N-(2-pyrimidinyl)amino]benzyl}-2,3-dioxopiperazine having a melting point of 85° to 90° C.

IR (KBr) cm$^{-1}$:
  $\nu_{C=O}$ 1735, 1665

Elementary analysis (for $C_{25}H_{25}N_5O_5$) Calcd. (%) C: 63.15, H: 5.30, N: 14.73; Found (%) C: 63.22, H: 5.38, N: 14.62.

NMR (CDCl$_3$) ppm values:
  3.40 (4H, s, piperazine ring CH$_2 \times$2)
  4.17 (2H, s, CH$_2 \times$1)
  4.63 (4H, s, CH$_2 \times$2)
  5.25 (2H, s, CH$_2 \times$1)
  6.75 (1H, t, J=5.0 Hz, pyrimidine ring H$\times$1)
  7.22 (5H, s, benzene ring H$\times$5)
  7.28 (4H, s, benzene ring H$\times$4)
  8.34 (2H, d, J=5.0 Hz, pyrimidine ring H$\times$2)
  9.82 (1H, bs, carboxylic acid H$\times$1)

EXAMPLE 4

In 10 ml of ethyl mercaptan was dissolved 1.0 g of 1-benzyl-4-{4-[N-pivaloyloxymethyl-N-(2-pyrimidinyl)amino]benzyl}-2,3-dioxopiperazine, and 0.01 ml of 5.7 N hydrogen chloride-dioxane solution was added thereto, after which the resulting mixture was subjected to reaction at room temperature for 3 hours. After the completion of the reaction, the reaction mixture was distilled under reduced pressure, and 50 ml of diisopropyl ether was added to the crystals thus obtained, after which the resulting crystals were filtered. The crystals thus obtained were recrystallized from isopropyl alcohol to obtain 0.8 g (86.8% yield) of white crystalline 1-benzyl-4-{4-[N-ethylthiomethyl-N-(2-pyrimidinyl)amino]benzyl}-2,3-dioxopiperazine having a melting point of 144° C.

IR (KBr) cm$^{-1}$:
  $\nu_{C=O}$ 1670

Elementary analysis (for $C_{25}H_{27}N_5O_2S_1$) Calcd. (%) C: 65.05, H: 5.89, N: 15.17; Found: (%) C: 65.02, H: 5.84, N: 15.12.

NMR (CDCl$_3$) ppm values:
  1.14 (3H, t, CH$_3 \times$1)
  2.53 (2H, q, CH$_2 \times$1)
  3.39 (4H, s, piperazine ring CH$_2 \times$2)
  4.62 (4H, s, CH$_2 \times$2)
  5.15 (2H, s, CH$_2 \times$1)
  6.57 (1H, t, pyrimidine ring H$\times$1)
  7.23-7.27 (9H, m, benzene ring H$\times$9)
  8.25 (2H, d, pyrimidine ring H$\times$2)

In the same manner as above, the following compound was obtained:

1-Benzyl-4-{4-[N-phenylthiomethyl-N-(2-pyrimidinyl)amino]benzyl}-2,3-dioxopiperazine Melting point: 64° to 65° C. (recrystallized from isopropyl alcohol)

IR (KBr) cm$^{-1}$:
  $\nu_{C=O}$ 1670

Elementary analysis (for $C_{29}H_{27}N_5O_2S_1$) Calcd. (%) C: 68.34, H: 5.34, N: 13.74; Found (%) C: 68.36, H: 5.32, N: 13.71.

NMR (CDCl$_3$) ppm values:
  3.33 (4H, s, piperazine ring CH$_2 \times$2)
  4.61 (2H, s, CH$_2 \times$1)
  4.65 (2H, s, CH$_2 \times$1)
  5.50 (2H, s, CH$_2 \times$1)
  6.60 (1H, t, pyrimidine ring H$\times$1)
  6.98-7.28 (14H, m, benzene ring H$\times$14)
  8.30 (2H, d, pyrimidine ring H$\times$2)

EXAMPLE 5

In 40 ml of N,N-dimethylformamide was dissolved 3.0 g of 1-benzyl-4-[4-(2-pyrimidinylamino)benzyl]-2,3-dioxopiperazine, and 0.372 g of sodium hydride (purity 52%) was added thereto, after which the resulting mixture was subjected to reaction at 80° C. for 30 min. with stirring. The reaction mixture was then cooled, and 0.72 ml of chloromethylmethylsulfide was added thereto, after which the resulting mixture was subjected to reaction at 50° to 60° C. for 2 hours. After the completion of the reaction, the reaction mixture was distilled under reduced pressure and the residue thus obtained was extracted with chloroform and then washed with water. The solution thus obtained was dried over anhydrous magnesium sulfate, and the solvent was then removed by distillation under reduced pressure. The crystals thus obtained were recrystallized from isopropyl alcohol to obtain 3.0 g (86.45% yield) of white crystalline 1-benzyl-4-{4-[N-methylthiomethyl-N-(2-pyrimidinyl)amino]benzyl}-2,3-dioxopiperazine having a melting point of 156° C.

IR (KBr) cm$^{-1}$:
  $\nu_{C=O}$ 1670

Elementary analysis (for $C_{24}H_{25}N_5O_2S_1$) Calcd. (%) C: 64.41, H: 5.63, N: 15.65; Found (%) C: 64.38, H: 5.61, N: 15.60.

NMR (CDCl$_3$) ppm values:
  2.10 (3H, s, CH$_3 \times$1)
  3.40 (4H, s, piperazine ring CH$_2 \times$2)

4.63 (4H, s, CH$_2$×2)
5.15 (2H, s, CH$_2$×1)
6.58 (1H, t, pyrimidine ring H×1)
7.10–7.35 (9H, m, benzene ring H×9)
8.26 (2H, d, pyrimidine ring H×2)

In the same manner as above, the following compound was obtained:

1-Benzyl-4-{4-[N-isopropylthiomethyl-N-(2-pyrimidinyl)amino]benzyl}-2,3-dioxopiperazine.

Melting point: 135° C. (recrystallized from isopropyl alcohol)

IR (KBr) cm$^{-1}$:
$\nu_{C=O}$ 1670

Elementary analysis (for C$_{26}$H$_{29}$N$_5$O$_2$S$_1$) Calcd. (%) C: 65.66, H: 6.14, N: 14.72; Found (%) C: 65.64, H: 6.12, N: 14.68.

NMR (CDCl$_3$) ppm values:
1.25 (6H, d, CH$_3$×2)
2.97 (1H, q, CH×1)
3.37 (4H, s, piperazine ring CH$_2$×2)
4.63 (4H, s, CH$_2$×2)
5.16 (2H, s, CH$_2$×1)
6.56 (1H, t, pyrimidine ring H×1)
7.22–7.27 (9H, m, benzene ring H×9)
8.26 (2H, d, pyrimidine ring H×2)

EXAMPLE 6

Based on Examples 1 to 3, any starting materials were selected to obtain the compounds shown in Table 4.

Note:
(1) In Table 4, IPA=isopropyl alcohol, IPE=diisopropyl ether, AcOEt=ethyl acetate, and Et$_2$O=diethyl ether.
(2) In the "Process" columns, the word "Pro." number refers to the process number stated in the description of the specification, and the compound referred to in the line in which the "Pro." number appears was synthesized in the same manner as in the Example mentioned hereinbefore concerning the said process, or according to the method described in the specification based on said Example.
(3) In the "Recrystallization Solvent" column, the term "Column" means that the product was purified by a column chromatography.

TABLE 4

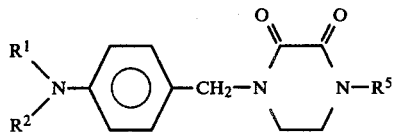

| R$^6$ | U | R$^7$ | m.p. (°C.) | Recrystallization Solvent | Process |
|---|---|---|---|---|---|
| H | O | —CH$_3$ | 138–140 | AcOEt | Pro. 4 |
| H | O | —C$_2$H$_5$ | 135–138 | AcOEt—Et$_2$O | Pro. 4 |
| H | O | —CH$_2$CH(CH$_3$)$_2$ | 145 | AcOEt | Pro. 4 |
| H | O | —C(=O)(CH$_2$)$_{16}$CH$_3$ | 116 | AcOEt | Pro. 4 |
| H | O | —CH$_2$CH(OH)CH$_2$OH | 75–83 | CH$_2$Cl$_2$—IPE | Pro. 5 |
| H | O | —CH$_2$CH$_2$N(CH$_2$CH$_2$OH)$_2$ | oil IR(neat)cm$^{-1}$: $\nu_{C=O}$ 1650 | Column | Pro. 5 |
| H | O | —CH(CH$_3$)$_2$ | 147 | IPA | Pro. 4 |

PREPARATION EXAMPLE 1

Per one capsule, 100 mg of 1-benzyl-4-{4-[N-methoxymethyl-N-(2-pyrimidinyl)amino]benzyl}-2,3-dioxopiperazine, 50 mg of milk sugar, 48 mg of corn starch and 2 mg of magnesium stearate were mixed, and capsules were filled with the resulting mixture, to obtain a capsule drug.

PREPARATION EXAMPLE 2

Per one tablet, 250 mg of 1-benzyl-4-{4-[N-ethoxymethyl-N-(2-pyrimidinyl)amino]benzyl}-2,3-dioxopiperazine, 50 mg of milk sugar, 38 mg of corn starch, 10 mg of polyvinyl pyrrolidone and 2 mg of magnesium stearate were mixed, and the resulting mixture was formed into tablets in the conventional manner to obtain a tablet drug.

What is claimed is:

1. A compound represented by the formula or a salt thereof, wherein either R$^1$ or R$^2$ represents pyrimidinyl and the other represents a C$_{1-8}$alkyl group which may be substituted by at least one substituent selected from the group consisting of C$_{1-4}$alkoxy, acetyloxy, propionyloxy, butyryloxy, pivaloyloxy, stearoyloxy, carboxy-C$_{1-4}$alkoxy, hydroxy-C$_{1-4}$alkoxy, and di-C$_{1-14}$alkylamino-C$_{1-4}$alkoxy; and R$^5$ represents a hydrogen atom, a C$_{1-8}$alkyl or ar-C$_{1-4}$alkyl group.

2. The compound of claim 1, wherein R$^2$ is a C$_{1-8}$alkyl group which may be substituted by a C$_{1-4}$alkoxy group.

3. The compound of claim 2, wherein $R^5$ is a n-hexyl or benzyl group.
4. The compound of claim 3 which is 1-benzyl-4-[4-[N-methoxymethyl-N-(2-pyrimidinyl)amino]benzyl]-2,3-dioxopiperazine of the formula:
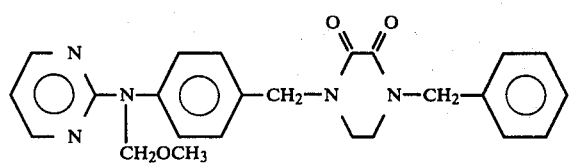
or its salt.
5. The compound of claim 3 which is 1-benzyl-4-[4-[N-ethoxymethyl-N-(2-pyrimidinyl)amino]benzyl]-2,3-dioxopiperazine of the formula:
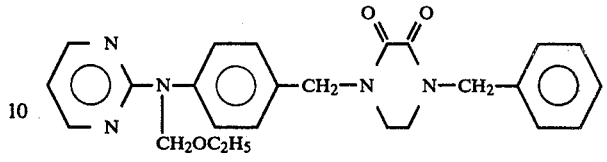
or its salt.
* * * * *